United States Patent [19]

Hattori et al.

[11] 4,108,891

[45] Aug. 22, 1978

[54] PROCESS FOR OXIDATION OF MONOSACCHARIDES

[75] Inventors: Kenichi Hattori, Musashino; Bunji Miya; Morio Matsuda, both of Wakayama; Mutsuo Ishii, Oomiya; Hisashi Saito, Higashimurayama; Hiroshi Watanabe, Kawagoe; Hidemitu Takizawa, Saitama, all of Japan

[73] Assignees: Kao Soap Co., Ltd.; Kawaken Fine Chemicals Co., Ltd., both of Tokyo, Japan

[21] Appl. No.: 765,203

[22] Filed: Feb. 3, 1977

[30] Foreign Application Priority Data

Sep. 21, 1976 [JP] Japan ................................. 51-113376

[51] Int. Cl.$^2$ ........................ C07C 51/26; C07C 59/17
[52] U.S. Cl. ..................................... 260/528; 252/447
[58] Field of Search ............................ 260/530 R, 528

[56] References Cited

U.S. PATENT DOCUMENTS

| | | | |
|---|---|---|---|
| 2,472,168 | 6/1949 | Mehltretter | 260/528 |
| 3,595,909 | 7/1971 | Sheldon | 260/528 |

FOREIGN PATENT DOCUMENTS 1,037,441  8/1958  Fed. Rep. of Germany ........... 260/528

*Primary Examiner*—Vivian Garner
*Attorney, Agent, or Firm*—Blanchard, Flynn, Thiel, Boutell & Tanis

[57] ABSTRACT

Monosaccharides are oxidized by an oxygen-containing gas in the presence of a special palladium-carbon catalyst which is prepared by adsorbing palladium on active carbon at a temperature lower than 60° C while the active carbon is suspended in an aqueous solution of an alkali metal hydroxide or carbonate and then reducing the palladium with formaldehyde.

11 Claims, No Drawings

PROCESS FOR OXIDATION OF MONOSACCHARIDES

BACKGROUND OF THE INVENTION

1. Field of the Invention

This invention relates to a process for oxidizing monosaccharides using an improved palladium catalyst.

Oxides of monosaccharides, for example, gluconic acid and its salts, are widely used as chelating agents, agents for washing objects made of glass and metals such as iron and aluminum, detergent builders, concrete additives, medicines, food additives and the like. Further, derivatives of these monosaccharide oxides are used in various fields, and especially δ-gluconolactone is well known as an effective food additive (for example, a baking powder, a bean curd coagulating agent and a pH adjusting agent).

2. Description of the Prior Art

At present, gluconic acid is prepared mainly by a fermentation process. Glucose can also be oxidized by a chemical oxidation process using bromine or the like, an electrolytic oxidation process and a catalytic oxidation process using a catalyst. Among the current industrial processes, the fermentation process can be performed most easily and simply and is most advantageous from the economic viewpoint. However, this process involves various difficulties. For example, separation of bacterial cells, control of the formation of by-products and disposal of the waste waters produced thereby are troublesome and are not easy to perform.

Preparation of gluconic acid by catalytic oxidation of glucose, as a typical example of oxidation reactions of monosaccharides, is disclosed in, for example, Japanese Patent Publication No. 7620/58. According to this known process, the oxidation is carried out in the presence of a catalyst of a noble metal such as platinum or palladium, under an alkaline condition. In this process, however, even though a 2 wt.% palladium-supported catalyst is used in a large amount such as about 10 wt.% (at least 0.05% by weight of palladium metal, based on the starting glucose), 7 hours are required for completion of the reaction.

In the process for preparing gluconic acid by catalytic oxidation of glucose, an alkaline substance must be added in order to neutralize the formed gluconic acid, and if no alkaline substance is added, the rate of oxidation of the glucose is very low or the oxidation does not progress at all. When glucose is allowed to stand still in an alkaline solution at room temperature, it is readily isomerized to fructose or the like (see Compiled Organic Chemistry, vol. 3, page 167; published by Asakura Shoten in 1957), and in this case, since conversion or oxidation of the thus-formed fructose to glucose is very difficult, the yield of gluconic acid is reduced. In order to prevent the occurrence of this undesirable conversion of glucose to fructose or the like, it is necessary to shorten the time during which glucose is present in an alkaline solution by shortening the time for the oxidation reaction of glucose.

SUMMARY OF THE INVENTION

We have discovered an economical process for preparing aldonic acids such as gluconic acid in high yields and high purities using a much reduced amount of a catalyst. In particular, we have discovered that a palladium-carbon catalyst which has not previously been used for oxidation processes, namely, a palladium-carbon catalyst formed by adsorbing palladium on activated carbon while the activated carbon is suspended in an aqueous alkaline solution and then reducing the palladium, is effective for oxidizing monosaccharides. Based on this discovery, we have now completed this invention.

More specifically, in accordance with this invention, there is provided a process for oxidizing monosaccharides with an oxygen-containing gas, in the presence of a palladium-carbon catalyst prepared by adsorbing palladium on activated carbon at a temperature lower than 60° C while the activated carbon is suspended in an aqueous solution of an alkaline substance having the formula MOH or $M_2CO_3$, in which M is an alkali metal, and then reducing the palladium with formaldehyde.

According to one embodiment of the process of this invention, a palladium-carbon catalyst, prepared as described in detail hereinafter, is added to an aqueous solution of glucose, and oxygen or an oxygen-containing gas is blown into the aqueous solution at 30° to 60° C under agitation, and simultaneously with the blowing-in of the oxygen or the oxygen-containing gas, an aqueous solution of an alkaline substance such as sodium hydroxide is added dropwise to the liquid reaction mixture. Since gluconic acid is formed as the reaction advances, the alkaline substance is added in an amount sufficient to neutralize the thus-formed acid. The rate of the dropwise addition of the alkaline substance is controlled to maintain the pH of the liquid reaction mixture at 8 to 11, preferably 9 to 10. The advance of the reaction is confirmed by the amount consumed of the alkaline substance. After completion of the reaction, the catalyst is removed by filtration and an aqueous solution of an alkali metal salt of gluconic acid is thus obtained.

The content of the gluconic acid salt is at least 97 wt.%, based on all of the substances, other than water, present in the thus-recovered aqueous solution.

In view of the reaction rate, the conversion and the degree of coloring, it is preferred to use monosaccharides of the aldose type, such as glucose, mannose, galactose and xylose, etc.

The product recovered by removing the catalyst from the reaction mixture can be used for various purposes as it is or after it has been concentrated or crystallized. If it is desired to obtain a product having a higher purity, the thus-recovered product can be purified by a conventional method.

The catalyst that is used in this invention can be prepared, for example, in the following manner.

Activated carbon is suspended in an aqueous solution of an alkaline substance, such as sodium hydroxide, and a palladium salt, such as palladium chloride, is added to the suspension which is maintained at a temperature lower than 60° C, preferably at 30° to 50° C, thereby to adsorb the palladium salt on the activated carbon. When this adsorption operation is carried out at a temperature lower than 30° C, a long time is required for completion of the adsorption. Accordingly, it is preferred that the adsorption operation be carried out at a temperature of 30° to 50° C. Then, formalin is added to the suspension as a reducing agent, and the palladium supported on activated carbon is reduced at a temperature in the range of from 30° C to the boiling point of the mixture. Then, the supported catalyst is recovered by filtration and washed with water. The thus-prepared catalyst is used for the oxidation reaction as it is or after drying same.

Salts such as palladium chloride and palladium nitrate can be used as the palladium salt in this invention. However, since these salts scarcely completely dissolve in water, it is preferred to dissolve these salts completely by the addition of a mineral acid, such as hydrochloric acid and nitric acid, or a salt, such as sodium chloride, and use them in the form of chloropalladic acid or a salt thereof.

In the palladium-carbon catalyst that is used in this invention, the amount of palladium supported on carbon is from 0.5 to 10% by weight, preferably 2 to 6% by weight, calculated as palladium metal, based on the total weight of the catalyst.

As the alkaline substance used to make the aqueous alkaline suspension of the activated carbon, hydroxides or carbonates of alkali metals such as sodium, potassium and lithium are used, and they are added in such an amount that after complete adsorption of the palladium on the activated carbon, the pH of the suspension is maintained at a level of at least 9.

In preparing the catalyst that is used in the process of this invention, it is necessary that the adsorption of palladium on activated carbon should be carried out at a temperature lower than 60° C. However, in this invention, after the majority of palladium, for example, 95 wt.% of the total palladium, has been adsorbed on the activated carbon, it is permissible to adsorb the remainder of the palladium on the activated carbon at a temperature higher than the above critical level. In this invention, however, it is preferred that the palladium is adsorbed completely at as low a temperature as possible.

Various processes for obtaining palladium-carbon catalysts are known. Typical examples of these known processes are as follows:

(1) A process in which activated carbon is suspended in water, an aqueous solution of palladium chloride acidified by hydrochloric acid is added to the suspension to cause the palladium salt to be adsorbed on the activated carbon and the palladium salt is reduced by addition of sodium hydroxide and formalin (see Org. Syn. Collect., vol. III, page 686) (this process is illustrated in Comparative Example 1 given hereinafter).

(2) A process in which activated carbon is suspended in an aqueous solution of sodium bicarbonate, an aqueous solution of palladium chloride is added dropwise to the suspension at room temperature, the temperature is elevated to 90° to 95° C, this elevated temperature is maintained for at least 15 minutes to cause the palladium salt to be adsorbed on the activated carbon, and then the palladium salt is reduced to form a reduction catalyst (see U.S. Pat. No. 2,857,337) (this known process is illustrated in Comparative Example 2 given hereinafter).

(3) A process in which activated carbon is added to an aqueous solution of palladium chloride, the mixture is dried by evaporation to adsorb palladium chloride on the activated carbon, and the palladium chloride is reduced with hydrogen in water or in a vapor phase (see Handbook of Catalysts, page 549; published by Chijin Shokan in 1967).

(4) A process in which palladium is adsorbed on activated carbon in a buffer solution containing a phosphate or a borate as the main ingredient while maintaining the pH at a substantially constant level in the range of from 6 to 13 and then palladium is reduced according to customary procedures (Japanese Pat. No. 501,722).

As processes for preparing catalysts similar to the catalyst of this invention, the following processes can be mentioned:

(5) A process in which reduction is carried out by using, as the reducing agent, formic acid instead of the formalin used in this invention.

(6) A process in which reduction is carried out by using, as the reducing agent, sodium borohydride or hydrazine instead of the formalin that is used in this invention.

(7) A process in which activated carbon is added to an aqueous solution of potassium chloropalladate to cause the palladium to be adsorbed on the activated carbon in the absence of an alkaline substance and the palladium is then reduced with formalin and sodium hydroxide.

(8) A process in which an aqueous solution of palladium chloride is added to an ammoniacal suspension of activated carbon to cause the palladium to be adsorbed on the active carbon and then formalin and sodium hydroxide are added to effect reduction.

With respect to 5%-palladium catalysts prepared according to the foregoing processes, the palladium particle size was determined from the half width of the [1.1.1] plane of palladium according to X-ray diffraction procedures, and glucose was oxidized according to procedures of Example 1 given hereinafter and the reaction time and the saccharide residual ratio were measured.

As described hereinafter, in the catalyst that is used in this invention, the palladium particle size is 40 to 70 Å, the reaction time is about 2 hours and the saccharide residual ratio is lower than 2 wt.%. Corresponding data obtained with respect to the catalysts prepared by the foregoing processes (1) to (8) are as follows:

Catalyst prepared by process (1):
  Palladium particle size = 140 Å, reaction time = 14 hours, saccharide residual ratio = 8.3 wt.%

Catalyst prepared by process (2):
  Palladium particle size = 94 Å, reaction time = 4 hours, saccharide residual ratio = 3.6 wt.%

Catalyst prepared by process (3):
  The catalyst prepared by conducting reduction in water had a palladium particle size of 180 Å. In the catalyst prepared by conducting reduction in a vapor phase, the palladium was amorphous. Each catalyst had a low oxidation reaction rate.

Catalyst prepared by process (4):
  Palladium particle size = 30 Å, reaction time = 12 hours, saccharide residual ratio = 8.1 wt.%

Catalyst prepared by process (5):
  Palladium particle size = 74 Å, reaction time = 10 hours, saccharide residual ratio = 4.0 wt.%

Catalyst prepared by process (6):
  Each catalyst prepared by this process had a palladium particle size of 130 Å and was low in reactivity.

Catalyst prepared by process (7):
  Palladium particle size = 130 Å, reaction time = 10 hours, saccharide residual ratio 3.5 wt.%

Catalyst prepared by process (8):
  The palladium was amorphous and the reactivity was low.

Further, we changed the kind of the alkaline substance used for preparing the alkaline suspension of activated carbon and the adsorption temperature used in making the palladium adsorbed on activated carbon catalyst, and examined the time required for adsorption and the activity of the resulting catalyst.

More specifically, palladium and hydrochloric acid were dissolved in water, the amount of palladium being 1 mole per 3 moles of hydrochloric acid, to form an aqueous solution containing palladium at a concentration of 0.5 g/25 ml calculated as palladium metal. Separately, an alkaline substance as indicated below was added to water in an amount of 8 moles per mole of palladium, and 9.5 g of activated carbon was added to the aqueous solution and the suspension was maintained at 75° C or 40° C. Then, 25 ml of the above aqueous solution of palladium was added dropwise to the suspension under agitation to cause the palladium to be adsorbed on active carbon. The time required for the suspension to become colorless and for the palladium to be adsorbed completely was measured. Then, a catalyst was prepared from the suspension according to the procedure described in Example 1 given hereinafter. The palladium particle size was determined from the half width of the palladium [1.1.1] plane according to X-ray diffraction and the time required for the oxidation reaction conducted according to procedures of Example 1 given hereinafter was examined. The results obtained are shown in Table 1.

lytic activity. Accordingly, these catalysts cannot be put into practical use on an industrial scale economically.

This invention will now be described in detail by reference to the following Examples.

EXAMPLE 1

Palladium chloride in an amount corresponding to 0.5 g of palladium, calculated as palladium metal, was dissolved in an aqueous solution containing 1.2 ml of concentrated hydrochloric acid to form 25 ml of an aqueous solution of palladium chloride. To a separately formed suspension of 9.5 g of commercially available activated carbon (Shirasagi A manufactured by Takeda Yakuhin K.K.; the same being used in subsequent Examples) in 100 ml of water, there was added 6.3 g of sodium carbonate as the alkaline substance, and the mixture was agitated at room temperature for 1 hour. Then, the temperature of this mixture was maintained at 40° C and the above aqueous solution of palladium chloride was added to the mixture. The resulting mixture was agitated for 4 hours to adsorb palladium completely. Then, 1 ml of a 38% aqueous solution of formaldehyde (formalin) was added to the mixture, and the temperature was maintained at 85° ± 5° C for 1 hour to Table 1

| Alkaline Substance | Adsorbed at 75° C | | | | Adsorbed at 40° C | | | |
|---|---|---|---|---|---|---|---|---|
| | Adsorption Time (min) | Palladium Particle Size (Å) | Oxidation Time (hr) | Remarks | Adsorption Time (hr) | Palladium Particle Size (Å) | Oxidation Time (hr) | Remarks |
| KOH | <15 | 104 | 14.5 | comparison | 6 | 55 | 2.5 | this invention |
| NaOH | <15 | 115 | 14.0 | comparison | 4 | 55 | 2.0 | this invention |
| $K_2CO_3$ | <15 | 110 | 10 | comparison | 7 | 58 | 2.2 | this invention |
| $Na_2CO_3$ | <15 | 83 | 6 | comparison | 3 | 60 | 1.7 | this invention |
| LiOH | <15 | 89 | 16 | comparison | 1.0 | 45 | 2.0 | this invention |
| $NaHCO_3$ | <15 | 122 | 7.5 | comparison | 11 | 138 | 8.3 | comparison |

As will be apparent from the foregoing results, the properties of the catalyst, especially its activity, are influenced by the kind of alkaline substance used and the adsorption temperature during the step of adsorption of the palladium on the activated carbon. Surprisingly, it has been found that the durability of the catalyst activity, namely, its effectiveness for repeated use, is greatly influenced by the above two factors. This will readily be understood from the results obtained in the Examples given hereinafter.

The catalyst that is used in this invention is characterized by the features that the palladium is adsorbed on the activated carbon in the presence of an alkaline substance at a high concentration and at a temperature not exceeding 60° C over a relatively long time period. In the catalyst of this invention, the palladium particle size is in the range of from 40 to 70 Å, while in most of the catalysts prepared according to the conventional processes, as well as catalysts obtained by conducting adsorption of palladium at a high temperature (for example, 75° C) in the presence of an alkaline substance, crystals of palladium are well developed and the particle size is larger than 100 Å. Further, in some of the catalysts prepared according to the conventional processes, crystals did not grow and the palladium remained amorphous. Each of these comparative catalysts has an activity lower than the activity of the catalyst of this invention and is inferior in the durability of its cataeffect reduction. Then, the solid was recovered by filtration, washed with water and dried to obtain a 5% palladium-carbon catalyst, in which the palladium particle size was 60 Å.

A 2.5-liter capacity reaction vessel equipped with a stirrer, a thermometer, an oxygen blowing-in opening, an alkaline substance-dropping funnel and a pH electrode was charged with 1800 g of an aqueous solution containing 540 g (3 moles) of glucose and 2.7 g of the above catalyst (0.025% by weight based on glucose, calculated as palladium metal). The aqueous solution was maintained at 50° ± 5° C under agitation and oxygen gas was blown into the solution. A 40% aqueous solution of sodium hydroxide was gradually added to neutralize the gluconic acid that formed as the reaction progressed, so that the pH of the aqueous solution was maintained at 9.5 ± 0.2. The theoretical amount of the alkaline substance was consumed in 1.7 hours from the start of the reaction. The catalyst was removed by filtration to obtain 2110 g of a filtrate having a light yellow color (Gardner color scale of 1). A part of the filtrate was sampled and evaporated to dryness under reduced pressure. The sample was converted to a trimethylsilyl derivative with a trimethylsilylating agent and the content of gluconic acid and the saccharide residual ratio of glucose were determined by gas chromatography (hydrogen flame ion detector). It was found that the content of gluconic acid in the concentrated solid was 98.6 wt.% and the saccharide residual ratio was 0.8 wt.%.

While the remainder of the above filtrate was being agitated, 6 l of methanol was added thereto to crystallize out sodium gluconate. The sodium gluconate product was recovered by filtration and dried to obtain 609 g of white crystals having a purity higher than 99 wt.%. The yield was 94%.

EXAMPLE 2

A 5% palladium-carbon catalyst was prepared in the same manner as described in Example 1 except that 1.5 g of sodium hydroxide was used instead of the sodium carbonate used in Example 1. In this catalyst, the palladium particle size was 55 Å.

By using 2.7 g of the thus-obtained catalyst (0.025% by weight based on glucose, calculated as palladium metal), glucose was oxidized in the same manner as described in Example 1. Two hours were required for completion of the reaction and a colorless transparent liquid was obtained. The content of gluconic acid in the solid obtained by concentrating the liquid was 97.5 wt.% and the saccharide residual ratio was 1.2 wt.%.

EXAMPLE 3

Palladium chloride in an amount corresponding to 2.0 g of palladium, calculated as palladium metal, was dissolved in an aqueous solution containing 5 ml of concentrated hydrochloric acid to form 250 ml of an aqueous solution of palladium chloride. Separately, 25 g of sodium carbonate was added to a suspension of 98 g of commercially available activated carbon in 1 l of water, and the suspension was agitated for 1 hour at room temperature and the temperature was then maintained at 40° C. The above aqueous solution of palladium chloride was added to the suspension, and the mixture was agitated for 4 hours to effect adsorption of palladium. Then, 5 ml of a 38% aqueous solution of formaldehyde was added and the mixture was maintained at 85° ± 5° C for 1 hour to effect reduction. The solid was recovered by filtration, washed with water and dried to obtain a 2 wt.% palladium-carbon catalyst.

By using 27.0 g of the thus prepared catalyst (0.1% by weight based on glucose, calculated as palladium metal), an aqueous solution of glucose was oxidized at a temperature of 30° ± 3° C and a pH of 10.0 in the same manner as described in Example 1 except that air was used instead of the oxygen gas used in Example 1. The reaction was completed in 2.5 hours and a colorless transparent liquid was obtained. The content of gluconic acid in the solid obtained by concentration of the liquid was 98.0 wt.% and the saccharide residual ratio was 1.2 wt.%.

COMPARATIVE EXAMPLE 1

A catalyst was prepared according to the process disclosed in Org. Syn. Collect., vol. III, page 686. More specifically, palladium chloride containing 0.5 g of palladium, calculated as metallic palladium, was dissolved in an aqueous solution containing 1.2 ml of concentrated hydrochloric acid to form 25 ml of an aqueous solution of palladium chloride. A suspension of 9.5 g of commercially available activated carbon in 100 ml of water was heated at 80° C and the above aqueous solution of palladium chloride was added to the suspension to effect adsorption under an acidic condition. Then, 0.8 ml of a 37% aqueous solution of formaldehyde was added to the above liquid, and a 30% aqueous solution of sodium hydroxide was further added dropwise and the reaction was conducted at 80° C for 1 hour under a slightly alkaline condition. The solid was recovered by filtration, washed with water and dried to obtain a 5% palladium-carbon catalyst, in which the palladium particle size was 140 Å.

By using a 2.7 g of the thus-prepared catalyst (0.025% by weight based on glucose, calculated as palladium metal), glucose was oxidized in the same manner as described in Example 1. Fourteen hours were required for completion of the reaction, and a liquid reaction mixture having a brown color was obtained. The content of gluconic acid in the solid obtained by concentration of the liquid mixture was 81.3 wt.% and the residual saccharide ratio was 8.3 wt.%.

COMPARATIVE EXAMPLE 2

A catalyst was prepared according to the process disclosed in the specification of U.S. Pat. No. 2,857,337. More specifically, 0.233 g of palladium chloride was dissolved in 23 ml of water containing 0.1 g of concentrated hydrochloric acid. Separately, 13.5 g of commercially available activated carbon was suspended in 240 ml of water, and 23 ml of water was evaporated from the suspension and an aqueous solution of 6.7 g of sodium hydrogencarbonate in 50 g of water was added dropwise over a period of 5 minutes. Then, the suspension was cooled to room temperature (20° C), and the above palladium chloride solution was added dropwise to the suspension over a period of 30 minutes. Then, the temperature of the resulting suspension was elevated to 95° C and the suspension was maintained at this temperature for 20 minutes. Then, an aqueous formalin solution containing 1.7 ml of 37% formalin and 4.2 ml of water was added to the suspension and the mixture was maintained at 95° C for 30 minutes. The resulting suspension was cooled to 40° C and filtered to obtain 33 g of a 1% palladium-carbon catalyst in the wet state. In this catalyst, the diffraction intensity of palladium was weak because the amount of palladium on the carbon was small, and therefore, the palladium particle size could not be measured. However, it was construed that the palladium particle size of this catalyst was probably similar to the palladium particle size of the catalyst obtained in Comparative Example 3 prepared by increasing the amount of palladium on the carbon, namely 94 Å.

By using the total amount of the thus-prepared catalyst (33 g in the wet state; 0.025% by weight based on glucose, calculated as palladium metal), glucose was oxidized in the same manner as described in Example 1. For completion of the reaction, 5.0 hours were required, and a liquid reaction mixture having a light brown color was obtained. The content of gluconic acid in the solid formed by concentration of the liquid reaction mixture was 91.3 wt.% and the saccharide residual ratio was 4.7 wt.%.

COMPARATIVE EXAMPLE 3

A catalyst was prepared according to U.S. Pat. No. 2,857,337. More specifically, palladium chloride containing 0.5 g of palladium, calculated as palladium metal, was dissolved in an aqueous solution containing 1.2 ml of concentrated hydrochloric acid to form 25 ml of an aqueous solution of palladium chloride. A suspension of 9.5 g of commercially available activated carbon in 600 ml of water was boiled to evaporate about 100 ml of water. A solution of 35 g of sodium hydrogencarbonate in 400 ml of water was added to the above suspension of activated carbon over a period of 5 minutes. The suspension was cooled to room temperature (20° C) and the above aqueous solution of palladium chloride was added dropwise to this suspension over a period of 30 minutes at room temperature. Then, the temperature of the suspension was elevated to 90° C under agitation and the suspension was maintained at this temperature for 30 minutes. Then, 3 ml of a 18.5% aqueous solution of formalin was added to the suspension, and the mixture was maintained at 90° C for 30 minutes and then cooled to 40° C. The solid was recovered by filtration, washed with 1 l of water and dried to obtain a 5% palladium-carbon catalyst. In this catalyst, the palladium particle size was 94 Å.

By using 2.7 g of the thus-prepared catalyst (0.025% by weight based on glucose, calculated as palladium metal), glucose was oxidized in the same manner as described in Example 1. For completion of the reaction, 4.0 hours were required, and a liquid reaction mixture having a light brown color was obtained. The content of gluconic acid in the solid obtained by concentration of the liquid reaction mixture was 92.0 wt.% and the residual saccharide ratio was 3.6 wt.%.

COMPARATIVE EXAMPLE 4

Palladium chloride containing 2.0 g of palladium, calculated as palladium metal, was dissolved in an aqueous solution containing 5 ml of concentrated hydrochloric acid to form 250 ml of an aqueous solution of palladium chloride. A suspension of 98 g of commercially available activated carbon in 1 l of water was heated at 80° C and the above aqueous solution of palladium chloride was added thereto. Then, 5 ml of a 37% aqueous solution of formalin was added to the suspension, and while a 30% aqueous solution of sodium hydroxide was added dropwise to the suspension to maintain an alkaline state, the suspension was heated at 80° C for 1 hour. The solid was recovered by filtration, washed with water and dried to obtain a 2% palladium-carbon catalyst. The palladium particle size could not be measured in this catalyst because of a weak X-ray diffraction intensity of palladium, but from the results of Comparative Example 1, it was construed that the palladium particle size was probably about 140 Å in this catalyst.

By using 48.6 g of the thus-prepared catalyst (0.18% by weight based on glucose, calculated as palladium metal), an aqueous solution of glucose was reacted at a temperature of 30° ± 3° C and a pH of 10.0 in the same manner as described in Example 1 except that air was used instead of the oxygen gas employed in Example 1. Twenty one hours were required for completion of the reaction, and a liquid reaction mixture having a light brown color was obtained. The content of gluconic acid in the solid obtained by concentration of the liquid reaction mixture was 89.6 wt.% and the saccharide residual ratio was 5.3 wt.%.

COMPARATIVE EXAMPLE 5

By using 2.7 g of a commercially available 5% palladium-carbon catalyst (in which the palladium particles were amorphous) (0.025% by weight based on glucose, calculated as palladium metal), glucose was oxidized in the same manner as described in Example 1. Six hours were required for completion of the reaction, and a brown liquid reaction mixture was obtained. The content of sodium gluconate in the solid obtained by concentration of the liquid reaction mixture was 90.0 wt.% and the residual saccharide ratio was 4.5 wt.%.

EXAMPLE 4 AND COMPARATIVE EXAMPLE 6

The durability of the catalysts used in Example 1 and Comparative Example 3 were examined in the following manner.

By using 2.7 g of the catalyst (0.025% by weight based on glucose, calculated as palladium metal), glucose was oxidized in the same manner as described in Example 1. After completion of the reaction, the catalyst was separated from the reaction mixture by filtration, and the separated catalyst was used for the second reaction in the same manner. Thus, the reaction was repeated 20 times in the same manner. The results shown in Tables 2 and 3 were obtained.

Table 2

| Results Obtained According to This Invention | | | |
|---|---|---|---|
| Repetition Frequency (times) | Reaction Time (hrs.) | Reaction Product | |
| | | gluconic acid (%) | residual saccharide (%) |
| 1 | 1.7 | 98.6 | 0.8 |
| 2 | 1.7 | 98.7 | 0.8 |
| 3 | 2.0 | 97.3 | 1.2 |
| 4 | 1.7 | 98.0 | 1.0 |
| 5 | 1.8 | 97.2 | 0.8 |
| . | | | |
| 10 | 2.0 | 97.3 | 1.2 |
| . | | | |
| 15 | 2.5 | 98.2 | 1.4 |
| . | | | |
| 20 | 3.2 | 98.0 | 1.4 |

Table 3

| Results Obtained in Comparative Example | | | |
|---|---|---|---|
| Repetition Freqency (times) | Reaction Time (hrs.) | Reaction Product | |
| | | gluconic acid (%) | residual saccharide (%) |
| 1 | 4.0 | 92.0 | 3.6 |
| 2 | 4.5 | 93.2 | 2.8 |
| 3 | 5.0 | 92.1 | 3.7 |
| 4 | 6.5 | 92.1 | 4.3 |
| 5 | 8.0 | 91.3 | 4.0 |
| . | | | |
| 10 | 12 | 87.2 | 7.3 |
| . | | | |
| 15 | 18 | 84.0 | 10.5 |

From the foregoing results, it will readily be understood that according to this invention, the catalyst can be used repeatedly more than 20 times without requiring major prolongation of the reaction time and without great reduction of the purity of the resulting gluconic acid product, and that the process of this invention is very advantageous from the economic viewpoint.

EXAMPLES 5 AND 6

In the same manner as described in Example 1, 1250 g of an aqueous solution containing 250 g (1.38 moles) of galactose was oxidized by using 1.25 g (0.025 % by weight based on galactose, calculated as palladium metal) of the 5% palladium-carbon catalyst prepared in Example 1. For completion of the reaction, 1.7 hours were required, and a liquid reaction mixture having a light yellow color was obtained. The content of galactonic acid in the solid obtained by concentration of the liquid reaction was 98.5 wt.% and the saccharide residual ratio was 0.5 wt.%.

When the above procedures were repeated by using mannose instead of galactose, the reaction was completed in 1.5 hours. The content of mannoic acid in the resulting solid reaction product was 98.0 wt.% and the saccharide residual ratio was 0.8 wt.%.

EXAMPLE 7

In the same manner as described in Example 1, 1250 g of an aqueous solution containing 250 g (1.67 moles) of xylose was oxidized by using 1.25 g (0.025% by weight based on xylose, calculated as palladium metal) of the 5% palladium-carbon catalyst prepared in Example 1. The reaction was completed in 1.0 hours and a colorless liquid reaction mixture was obtained. The content of xylonic acid in the solid obtained by concentration of the reaction mixture was 98 wt.% and the saccharide residual ratio was 1.0 wt.%.

The embodiments of the invention in which an exclusive property or privilege is claimed are defined as follows:

1. In a process for oxidizing monosaccharides to carboxylic acid derivatives in which a monosaccharide is reacted with oxygen or an oxygen-containing gas, in the presence of a palladium-carbon catalyst, the improvement wherein: said catalyst has a palladium particle size in the range of from 40 to 70 Angstroms and is prepared by suspending activated carbon in an aqueous solution of an alkali metal hydroxide or carbonate, then adding an aqueous solution of a palladium salt to said suspension at a temperature of from 30° C to lower than 60° C to adsorb said palladium salt on said activated carbon, then adding an aqueous solution of formaldehyde to said suspension to reduce said palladium salt to palladium metal and then recovering the palladium-carbon catalyst from the suspension, the amount of said alkali metal hydroxide or carbonate in said suspension being sufficient to maintain the pH of said suspension at a value of at least 9 after adsorption of the palladium salt on the activated carbon has been completed.

2. A process according to claim 1 wherein the alkali metal is sodium, potassium or lithium.

3. A process according to claim 1 wherein the amount of said palladium supported on said activated carbon is 0.5 to 10% by weight, calculated as palladium metal.

4. A process according to claim 1 wherein said palladium salt is palladium chloride or palladium nitrate.

5. A process according to claim 1 wherein the monosaccharide is of the aldose type.

6. A process according to claim 5 wherein the monosaccharide is glucose.

7. A process according to claim 5 wherein the monosaccharide is galactose, xylose or mannose.

8. A process according to claim 1 wherein said monosaccharide is reacted with said oxygen-containing gas while adding an alkaline substance dropwise to maintain the pH of the reaction mixture at 8 to 11.

9. A process according to claim 1 wherein said suspension is maintained at a temperature of 30° to 50° C during addition of said aqueous solution of said palladium salt.

10. A process according to claim 1, in which oxygen or an oxygen-containing gas is blown into an aqueous solution of said monosaccharide having a temperature of from 30° to 60° C and containing said catalyst, while simultaneously agitating said liquid reaction mixture and continuously adding an aqueous solution of an alkali metal neutralizing agent to maintain the pH of the liquid reaction mixture at from 8 to 11 and to form an alkali metal salt of a carboxylic acid derivative of said monosaccharide.

11. A process according to claim 1 in which, during the step of reducing said palladium salt to palladium metal with said formaldehyde, the temperature of the suspension is maintained at from 30° C to the boiling point of the mixture.

* * * * *